US012685642B2

(12) United States Patent (10) Patent No.: US 12,685,642 B2
Dalla Pria et al. (45) Date of Patent: Jul. 21, 2026

(54) IMPLANT COMPONENT ASSEMBLY

(71) Applicant: WALDEMAR LINK GMBH & CO. KG, Hamburg (DE)

(72) Inventors: Paolo Dalla Pria, Udine (IT); Angelika Harndt, Berlin (DE); Alexander Etringer, Norderstedt (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 996 days.

(21) Appl. No.: 17/757,292

(22) PCT Filed: Dec. 15, 2020

(86) PCT No.: PCT/EP2020/086181
§ 371 (c)(1),
(2) Date: Jun. 13, 2022

(87) PCT Pub. No.: WO2021/122568
PCT Pub. Date: Jun. 24, 2021

(65) Prior Publication Data
US 2023/0033626 A1 Feb. 2, 2023

(30) Foreign Application Priority Data
Dec. 16, 2019 (EP) .................................... 19216469

(51) Int. Cl.
*A61F 2/30* (2006.01)
*A61F 2/40* (2006.01)
*A61F 2/46* (2006.01)
(52) U.S. Cl.
CPC ...... *A61F 2/30734* (2013.01); *A61F 2/30749* (2013.01); *A61F 2/4014* (2013.01);
(Continued)

(58) Field of Classification Search
CPC ............ A61F 2/4014; A61F 2002/3674; A61F 2002/4044; A61F 2002/3652
See application file for complete search history.

(56) References Cited

U.S. PATENT DOCUMENTS 5,653,764 A * 8/1997 Murphy ................ A61F 2/3609
623/23.15
6,974,483 B2 * 12/2005 Murray ............... A61F 2/30734
623/22.46
(Continued)

FOREIGN PATENT DOCUMENTS

EP 2777621 A1 9/2014
FR 2737107 A1 1/1997
FR 2925841 A1 7/2009

OTHER PUBLICATIONS

Extended European Search Report mailed Mar. 23, 2020, in connection with European Patent Application No. 19216469.7, filed Dec. 16, 2019, 6 pgs.

(Continued)

*Primary Examiner* — Megan Y Wolf
(74) *Attorney, Agent, or Firm* — Chiesa Shahinian & Giantomasi PC

(57) ABSTRACT

The present disclosure provides an implant component assembly for a joint replacement. The assembly comprises an implant component, the implant component including an interface part for attaching another implant component and an assembly channel. The assembly further comprises an assembly screw for securing the other implant component to the implant component, the assembly screw having a longitudinal axis, a screw head, and a screw shank and being insertable into the assembly channel. A screw retention unit of the assembly is configured for keeping the assembly (Continued)

screw within the assembly channel and allowing rotation of the assembly screw about the longitudinal axis.

13 Claims, 3 Drawing Sheets

(52) U.S. Cl.
CPC ............... *A61F 2002/30331* (2013.01); *A61F 2002/30332* (2013.01); *A61F 2002/30364* (2013.01); *A61F 2002/30433* (2013.01); *A61F 2002/30507* (2013.01); *A61F 2002/30604* (2013.01); *A61F 2002/30607* (2013.01); *A61F 2002/30617* (2013.01); *A61F 2002/30772* (2013.01); *A61F 2002/3082* (2013.01); *A61F 2002/4044* (2013.01); *A61F 2/4637* (2013.01)

(56) References Cited

U.S. PATENT DOCUMENTS 9,629,725 B2 * 4/2017 Gargac ................. A61F 2/4081

2003/0149485 A1 8/2003 Tornier
2007/0112430 A1 5/2007 Simmen et al.
2007/0156246 A1 * 7/2007 Meswania ................. A61F 2/40
623/19.12
2010/0023068 A1 1/2010 Bouttens et al.
2013/0261750 A1 * 10/2013 Lappin .............. A61B 17/8042
623/19.11
2018/0078377 A1 3/2018 Gargac et al.
2018/0161169 A1 * 6/2018 Cardon ................. A61F 2/4081

OTHER PUBLICATIONS

International Search Report and Written Opinion mailed Mar. 3, 2021, in connection with International Patent Application No. PCT/EP2020/086181, filed Dec. 15, 2020, 10 pgs.
Communication pursuant to Article 94(3) EPC mailed Apr. 20, 2023 in connection with European Patent Application No. 19216469.7, filed Dec. 16, 2019, 6 pgs.

* cited by examiner

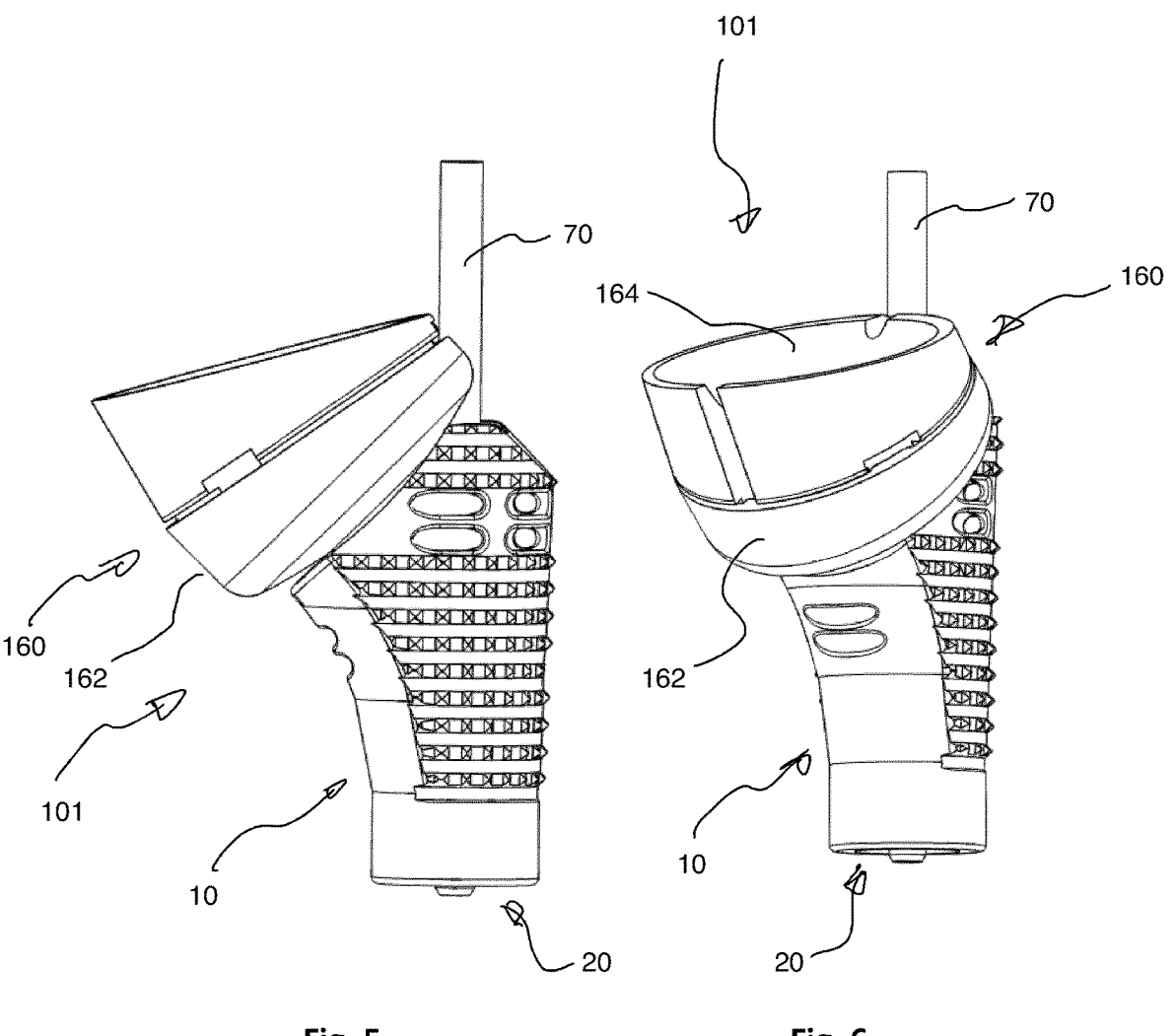
Fig. 5 Fig. 6

IMPLANT COMPONENT ASSEMBLY

CROSS-REFERENCE TO RELATED APPLICATIONS

This application is a national stage of International Patent Application Serial No. PCT/EP2020/086181, filed Dec. 15, 2020, which claims priority to European Patent Application No. 19216469.7, filed Dec. 16, 2019; the disclosures of all are incorporated herein by reference in their entirety.

TECHNICAL FIELD

The present disclosure relates to an implant component assembly employing an assembly screw and a screw retention unit for keeping the assembly screw movably attached to an implant component of the implant component assembly before assembly to another implant component. The present disclosure also relates to a method for pre-assembling an implant component assembly.

BACKGROUND OF THE INVENTION

Modular joint replacements are state of the art for replacing a native joint of a patient. The modularity of these implants allows to adapt their shape and dimension to the individual anatomical situation of the patient. This modularity is one of the reasons for the longevity and the success of joint replacements that are available for the treatment of deteriorated joints.

Although generally lasting over a decade while often providing a patient with the life and activity used to prior surgery, joint replacements may have to be replaced for several reasons. One of these reasons is wear of a joint replacement over time. Here, the objective is to make use of the modularity by limiting the replacement of implant components to components that have been worn off to a degree that they need to be exchanged.

Another reason that may make a revision of a joint replacement necessary is an infection of the tissue surrounding the implant. If the degree of infection allows for a partial exchange of a joint replacement, the modularity of an implant may also in this case be used advantageously in order to prevent the need for a revision of the entire implant component.

A replacement of individual implant components instead of the entire joint replacement is also advantageous in case of joint replacements for synovial joints that are primarily stabilized by soft tissue, i. e. ligaments and muscle tissue. For these joints, the exchange of individual implant components prevents luxation of the joint after surgery since the surgical procedure requires a smaller access than in case of a revision of at least the affected side of the joint replacement. As a result, preservation of the surrounding soft tissue is enhanced. Examples of such joints are knee joints, shoulder joints, ankle joints, and wrist joints.

However, the disassembly of individual components of a modular joint replacement often turns out to be tedious since it has to be performed through a small access opening created during the surgical procedure in order to preserve soft tissue structures. Further, the connection between implant components is made to last so as not to be the reason for a revision. As a result, it is often hard to disassemble implant components that have stayed implant over a long time.

In particular a tapered connection is a preferred type of a lasting connection used in joint replacements since joint components are generally loaded with compressive forces. These compressive forces act in an advantageous manner on this connection type and its self-locking properties. More specifically, the load applied during everyday use results in a tighter interlock between the implant components.

Nonetheless, the advantage of this type of connection may turn into a disadvantage during the exchange of an implant component while leaving the remaining implant components untouched. Not only that it is hard to separate this self-locking connection, there is also only limited space available for applying the force needed for the separation of the implant components.

SUMMARY OF THE INVENTION

Consequently, it has been an objective of the following disclosure to provide an implant component assembly or modular joint replacement that allows for an easy disassembly. In particular, it has been an objective to provide a mechanism that facilitates the disassembly of implant components in an environment of limited space to apply the force needed to disengage the connection of these implant components.

The solution of this objective is defined in the independent claims, wherein the dependent claims specify preferred embodiments.

The objectives from above have been addressed by providing an implant component assembly for a joint replacement. The assembly comprises an implant component that includes an interface part for attaching another implant component and an assembly channel. The assembly further comprises an assembly screw for securing the other implant component to the implant component, wherein the assembly screw has a longitudinal axis, a screw head, and a screw shank, and is insertable into the assembly channel. It also includes a screw retention unit configured for keeping the assembly screw within the assembly channel and allowing rotation of the assembly screw about the longitudinal axis.

The assembly screw secures the implant components to each other when being fastened. Since the screw retention unit keeps the assembly screw within the assembly channel while allowing rotation of the assembly screw about the longitudinal axis, the assembly screw does not have to be inserted separately but is instead inserted together with the implant component. This facilitates the assembly to another implant component, in particular if the other implant component is already placed inside the patient.

Further, the screw retention unit also retains the assembly screw within the assembly channel during disassembly, i.e. during loosening of the screw. In other words, the screw shank of the assembly screw is moving out of a threaded engagement with the other implant component. However, since the mobility of the assembly screw along the assembly channel is limited by the screw retention unit, the assembly screw also moves the implant component away from the other implant component due to the engagement of the assembly screw in the assembly channel of the implant component.

In other words, the screw retention unit of the implant component keeps or captures the assembly screw within the assembly channel, i.e. in both directions along the assembly channel. As a result, the retention unit prevents the assembly screw from falling out of the assembly channel while handling the implant component. Preferably, the retention unit provides a form fit to the screw that captures the screw but allows free movement of the screw in its rotational direction and a limited movement along its longitudinal axis.

Since the assembly screw is arranged for securing the implant component to another implant component, it is arranged to protrude from the assembly channel of the implant component and is preferably arranged to protrude at the interface part of the implant component.

For tightening or using the assembly screw, the assembly screw is accessible at the side of the screw head. This accessibility is provided by the assembly channel. In particular, the assembly channel is configured to accommodate a a tool for engaging the screw head in order to rotate the screw in either direction. As a result, the assembly channel is preferably extending from the interface part to a side of the implant component that is opposite to the interface part. The assembly channel has a longitudinal axis and is preferably straight. Nonetheless, the assembly channel may also be at least partly curved.

Further, the assembly screw may be produced so that it is in engagement with the screw retention unit, e.g. by additive manufacturing or mounting the assembly screw inside the assembly channel.

Preferably, the screw retention unit includes a screw seat for supporting the screw head, the screw seat comprising a through hole for accommodating the screw shank.

A screw seat is a simple structural feature to limit the movement of the assembly screw in relation to the implant component and more specifically the assembly channel in at least one direction. The screw seat at least supports the screw head when the implant component is assembled to the other implant component. Thus, the screw seat supports the screw head where the assembly screw is tightened.

Further, the screw seat may also act in both directions, i.e. limit the ability of the assembly screw along both directions of the assembly channel. In particular, the screw seat engages the screw shank and preferably a portion of the screw shank having a reduced diameter in comparison to a threaded portion of the screw shank. This portion having a reduced diameter is, thus, situated between the threaded portion of the screw shank and the screw head.

It is preferred that the assembly channel comprises an accommodation portion and the screw seat is insertable into the accommodation portion.

In this case, the screw seat is insertable, i.e. is a separate part or component instead of a component that is formed integrally with the implant component. As a result, the screw retention unit can be assembled by placing the screw head of the assembly screw within the assembly channel before inserting and securing the screw seat to the implant component. Preferably, the screw seat is formed as a screw insert mounted in the accommodation portion of the assembly channel. For this, the screw seat may comprise a tool engagement interface to handle and/or fixate the screw seat to the implant component.

Accordingly, such a combination of features provides an easy way to assemble the screw retention unit. This facilitates manufacturing and the quality of the screw retention unit since the parts of the implant component assembly are produced separately before being assembled rather than having to be produced at the same time such as by additive manufacturing. In other words, the screw seat is not integrally formed with the implant component.

Further, the screw seat is preferably fixed within the accommodation portion by a form fit, friction fit, and/or welding.

As form fit for fixing the screw seat, a snap-fit arrangement may be employed. Alternatively, a friction fit may be used, preferably by causing a press fit between the screw seat and the accommodation portion of the screw channel.

Nonetheless, preferably, the screw seat is assembled and fixed to the implant component via a threaded engagement, i. e. it is fixed to the implant component via a friction fit. This arrangement allows for an assembly as well as a disassembly of the screw seat. Independent of its fixation, the screw seat may act as a limitation for the movements of the screw relative to the implant component in either or both directions along the assembly channel (longitudinal axis of the screw or assembly channel).

In case of the screw seat supporting the screw head of the assembly screw in a mounted state of the implant components, the entire screw shaft is configured to pass through the through hole of the screw seat. In case of the screw seat limiting the freedom to move of the assembly screw in both directions, only a portion of the screw shaft is allowed to pass in an assembled state of the screw shaft and the assembly screw so that at one and of the range of longitudinal movement the screw head is supported by the screw seat and at the other end of the range of longitudinal movement, a distal portion of the screw shaft having a larger diameter about us on the side of the screw seat opposite to the side, where the screw head is supported. For the latter, the assembly screw is preferably retained in the screw seat by a form fit or friction fit.

It is particularly preferred that the screw retention unit further comprises a screw stop, the screw stop preferably being formed as a step of the assembly channel.

In this case, the screw head of the assembly screw on the side opposite to the side of the screw shank abuts at the screw stop when being moved in this direction inside the assembly channel. In other words, the screw stop limits the movement of the assembly screw further into the assembly channel, i.e. the direction the assembly screw moves to during loosening of the screw. In an assembled state of the implant component assembly, it is the end face of the assembly screw's head that faces the screw stop. In contrast, the end face of the screw head where the shank protrudes faces a screw seat.

This configuration results in the assembly screw pushing the implant component away from the other implant component. As a result, the disassembly of the implant components is easier to handle and on top is performed in a very controlled manner without using any sudden force that bears the risk of tissue damage.

The screw stop is preferably formed as a step in the assembly channel, i.e. decrease in diameter of the assembly channel in a direction pointing away from the interface part. As a result, the diameter of the assembly channel on the interface side of the step is big enough to accommodate the screw head of the assembly screw, whereas the diameter on the opposite side is smaller so that the screw head is not able to pass. Nonetheless, the smaller diameter of the assembly channel is dimensioned to allow a fastening tool to pass and engage the assembly screw for fastening or loosening.

Accordingly, a diameter of the assembly channel may be smaller than a diameter of the screw head so that the assembly screw is not able to exit through the end of the assembly channel on the side opposite to the side, where the interface part is located.

The step is preferably integral to the assembly channel but may also be inserted and fixed as a separate part. In this respect, it should be noted that the screw seat as well as the screw stop are either or both preferably be formed to provide a contact with the assembly screw via a surface contact rather than a line or point contact.

In the configuration using the screw stop, the movement of the assembly screw in the other direction is preferably limited by a screw seat as described above, preferably an insertable screw seat. The screw seat and the screw stop together form a capture portion for limiting the move ability of the screw head along the longitudinal axis of the assumption and, thus, the movement of the assembly screw.

Accordingly, the capture portion is dimensioned so that the extension of the space in the longitudinal direction between the screw seat and the screw stop is larger than the extension of the screw head in the longitudinal direction.

The skilled person will appreciate that the extension of the capture portion in the longitudinal direction of the assembly channel and the extension of the screw head in the longitudinal direction of the screw is measured so that they relate to each other (e. g. at their maximum extension).

Preferably, the interface part of the implant component comprises a tapered interface surface for mounting the other implant component, the tapered interface surface preferably defining a recess.

In particular when being configured as a tapered connection, the assembly screw allows on the one hand to use a predefined force to lock the tapered connection and on the other hand allows to disengage the tapered connection during disassembly of the implant components.

In other words, the interface part is configured as a tapered connection. It may also alternatively or additionally be formed as a connection with a cylindrical interface surface. Preferably, the configuration with a tapered connection is configured as a conical connection. If formed as a recess, the interface surface forms a circumferential wall facing radially inwards. Likewise, if formed as a protrusion, the interface surface forms a circumferential wall facing radially outwards.

Independent of being tapered or cylindrical, the longitudinal axis of the assembly screw in an assembled state is preferably substantially parallel to the longitudinal axis of the interface part, i. e. the longitudinal axis that basically defines a vector for bringing the implant components into contact with each other. It should be noted that the longitudinal axis of the interface part may be parallel or inclined in relation to a longitudinal axis of the implant component.

Further if formed as a recess, the mouth of the assembly channel (the exit opening of the interface), is located at the bottom of the recess, whereas, if formed as a protrusion, the mouth of the assembly channel is located at the tip of the protrusion.

Further, being formed as a recess results in a more compact build of the implant component comprising the assembly channel.

Preferably, the screw shank of the assembly screw has a threaded portion and an unthreaded portion, the unthreaded portion being located between the threaded portion and the screw head.

This configuration of an assembly screw may be used in connection with the screw seat to limit the movement of the assembly screw in both directions of the assembly channel. In a case that includes both, i. e. a screw seat and a screw stop, such a design of the assembly screw has the advantage to reliably prevent any contact of the assembly screw with the through hole of the screw seat and, thus, any influence on the interface part when being connected to and the interface part of another important component. Further, the unthreaded portion is preferably cylindrical.

It is also preferred that the implant component further comprises another interface part for attaching a joint member, the other interface part being formed as a recess, preferably a tapered recess, and even more preferably including a joint assembly channel dimensioned for accommodating a joint fixation screw for securing the joint member.

If the assembly channel has a smaller diameter than the screw head of the assembly screw, this facilitates having an implant component with multiple interfaces such as the interface part for attaching a joint member. Naturally, the joint assembly channel may also be configured like an assembly channel according to the previous description.

Preferably, the implant component further comprises at least one suture hole and/or at least one suture groove for securing soft tissue to the implant component.

Here, the attachment of soft tissue structures is facilitated using above-noted structural features. Since the size of the assembly channel is smaller since only a fastening tool for assembling the implant component to another implant component has to be passed through this channel, it is possible to provide the implant component with more structural features formed as holes or recesses without affecting the strength of the implant component that is necessary to withstand the forces acting on the implant component assembly after implantation.

Further, the implant component may comprise a handling tool engagement recess for engaging a handling tool for handling the implant component during a surgical procedure.

For the same reason as the one presented above, a handling tool engagement recess can be provided. Further, such a recess or a handling tool in engagement with this recess may assist in fastening or loosening the assembly screw by supporting the implant component during application of torque to the implant component. Preferably, the handling tool engagement recess is provided at the proximal side of the implant component for an easier access.

Preferably, the assembly screw comprises a tool interface recess formed for an engagement of a fastening tool in a rotational direction about the longitudinal axis of the assembly screw.

The disclosure further provides a method for pre-assembling an implant component assembly of a joint replacement as described above. The method comprises the steps of providing an implant component that includes an assembly channel and an interface part, wherein the assembly channel is formed as a through hole and extends from a proximal side of the implant component to the interface part; providing a screw seat, wherein the screw seat comprises a through hole; providing an assembly screw having a longitudinal axis, a screw head, and a screw shank; inserting the screw shank of the assembly screw into the through hole of the screw seat; inserting the assembled screw seat and assembly screw with the screw head first into an accommodation portion of the assembly channel from the side of the interface part; and fixing the screw seat within the accommodation portion of the assembly channel.

Preferably, the method further comprises the steps of providing another implant component, in particular an implant stem, the other implant component comprising an interface part corresponding to the interface part of the implant component and a threaded hole for engagement with the assembly screw; connecting the implant components via their interface parts; and securing the implant components to each other via tightening the assembly screw.

SHORT DESCRIPTION OF THE DRAWINGS

The following figures illustrate preferred embodiments of the present invention. These embodiments are not to be construed as limiting but merely for enhancing the understanding of the invention in context with the following description. In these figures, same reference signs refer to features throughout the drawings that have the same or an equivalent function and/or structure. This particularly applies to reference signs that are identical in the last two digits, wherein the preceding digits denote the embodiment. It is to be noted that a repetitive description of these components is generally omitted for reasons of conciseness of the description.

FIG. 5 shows a side view of another embodiment of an implant component assembly of a joint replacement; and FIG. 6 is a three-dimensional view of the implant component assembly shown in FIG. 5.

DETAILED DESCRIPTION OF PREFERRED EMBODIMENTS

The skilled person will appreciate that a joint replacement component comprising an implant component assembly may be arranged on only one side of a synovial joint, i. e. it may replace only one side of a synovial joint. In this case, the joint replacement component represents only a partial replacement of the joint, a so-called hemi-arthroplasty. Nonetheless, frequently a joint replacement is concerned with a replacement of the joint surfaces on both sides of a joint. Further, either or both sides of a joint replacement may comprise an assembly of several implant components, such as a joint component and an anchoring component.

Figures 1, 2, 3:
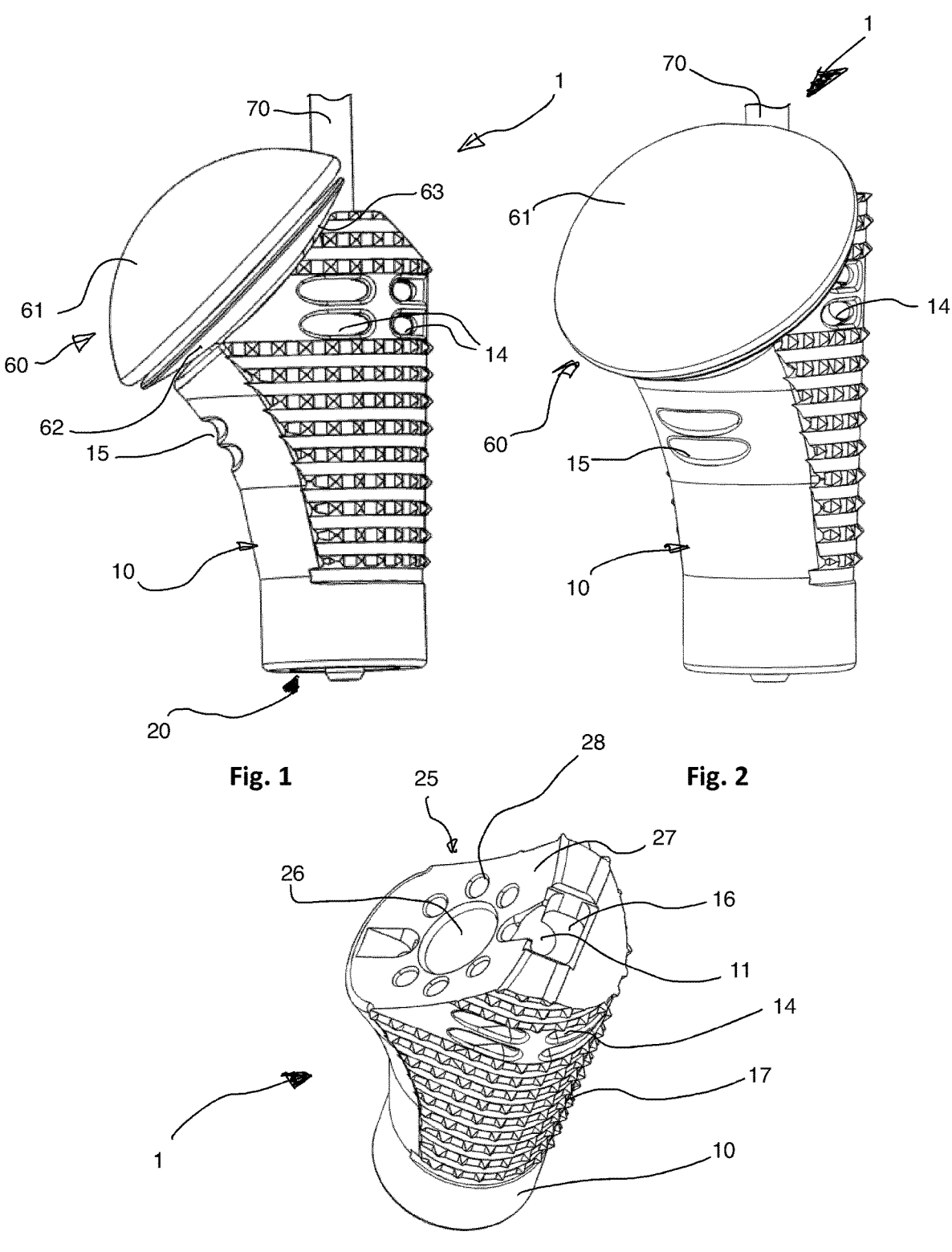
FIG. 1 illustrates a side view of an embodiment of an implant component assembly of a joint replacement.
FIG. 2 illustrates a three-dimensional view of the implant component assembly shown in FIG. 1 from a different perspective.
FIG. 3 is a three-dimensional view of an implant component showing an interface part of this component.

FIGS. 1 and 2 illustrate an exemplary embodiment of a joint replacement component 1. The joint replacement component 1 comprises a first implant component 10 and a joint member 60. As shown in FIG. 1, the joint member 60 may comprise a joint part 61 and an intermediate part 62. The joint part 61 and the intermediate part 62 are attached to each other by any of the ways described above. The joint member 60 is mounted to the first implant component 10, i.e. in the present embodiment the joint part 61 comprising the joint surface is mounted to the implant component 10 via the intermediate part 62. The intermediate part 62 may serve as an adapter to optimize the position and orientation of the joint part 61 comprising the joint surface. Such an intermediate part may be fixed to the first implant component 10 via a fastening screw as will be explained in more detail further below. This allows for a particularly reliable connection between the first implant component 10 and the intermediate part 62. The arrangement with an intermediate part 62 also prevents loosening of a tapered connection to the joint part 61 since the joint surface is arranged close to the tapered connection so that there is essentially no lever arm that may cause such a loosening. Accordingly, there is no hole present in the joint surface that would otherwise be necessary to fix the joint part 61 via a screw. The adapter may also comprise suture holes (not shown).

Nonetheless, the joint member 60 may also be directly attached to the first implant component 10.

The first implant component 10 has a proximal end and a distal end. The proximal end of the first implant component 10 is the end closer to the location of the joint or joint surfaces of the joint replacement, whereas the distal end is on the side opposite to the side, where the joint is located.

As will be described in more detail further below, the first implant component 10 is preferably configured for the attachment of soft tissue, whereas a second implant component 50 is configured for anchoring the implant in bone tissue. This configuration is particularly advantageous in case of a shoulder joint replacement.

For connecting the joint member 62, the first implant component 10 comprises at its proximal end a second interface part 25. The second interface part 25 is shown in more detail without the joint member 60 in FIG. 3. As illustrated in this figure, the second interface part 25 may include a mounting hole defined by an interface surface 26. In the exemplary embodiment, the interface surface 26 forms a tapered recess (cf. FIG. 4). Accordingly, the joint member 60 comprises a tapered protrusion (not shown). Together, the tapered recess and the tapered protrusion establish a tapered connection between the joint member 60 and the first implant component 10 upon assembly. Although the second interface part 25 and the corresponding interface part of the joint member 60 may also be defined by cylindrical interface surfaces, tapered interface surfaces are preferred, in particular conical interface surfaces. Such a tapered connection has proven to be easily assembled and to be reliable during use of the implant. Naturally, it is also possible to switch the recess and the protrusion of the interface parts so that the recess is formed at the joint member 60 and the protrusion is formed at the first implant component 10.

As illustrated in the exemplary embodiment of FIG. 3, the second interface part may further comprise a concave interface surface 27. More clearly shown in the side views of FIGS. 1 and 4, the joint member 60 comprises a convex interface surface 63 that is formed so as to correspond to the concave interface surface 27 of the second interface part 25. Since the exemplary embodiment illustrated in FIGS. 1 to 4 (and preferably also the embodiment illustrated in FIGS. 5 to 6) employs a tapered connection between the joint member 60 and the first implant component 10, the convex interface surface 63 of the joint member 60 faces the concave interface surface 27 of the first implant component at a distance, i.e. these surfaces are not in contact, so that the functionality of the tapered connection is not impaired.

Further, the second interface part 25 shown in FIG. 3 comprises an array of indexing holes 28. These indexing holes are arranged on a circle. The center of the circle is located along the longitudinal axis defined by the interface surface 26, i.e. the rotational axis of the conical taper of this exemplary embodiment. The indexing holes 28 may provide a locking mechanism for the orientation of the joint member 60 about this rotational axis. Since the joint surface of the joint member 60 is rotational symmetric to the longitudinal axis of the tapered connection, the joint member 60 may comprise a corresponding indexing pin (not shown) to prevent any rotation of the joint member 60 about the longitudinal axis of the tapered connection. This indexing prevents an unintended relative rotation between these two implant components 10 and 60 and, thus, helps against an unintended loosening of the connection of these implant components.

In another embodiment, the joint member 60 may be an eccentric joint member, i. e. the center of such a joint member is offset from the center of the connection between the two implant components. In such an embodiment, the indexing allows to adjust and fixate the joint member 60 relative to the first implant component 10 at a predetermined position and orientation.

Figure 4:
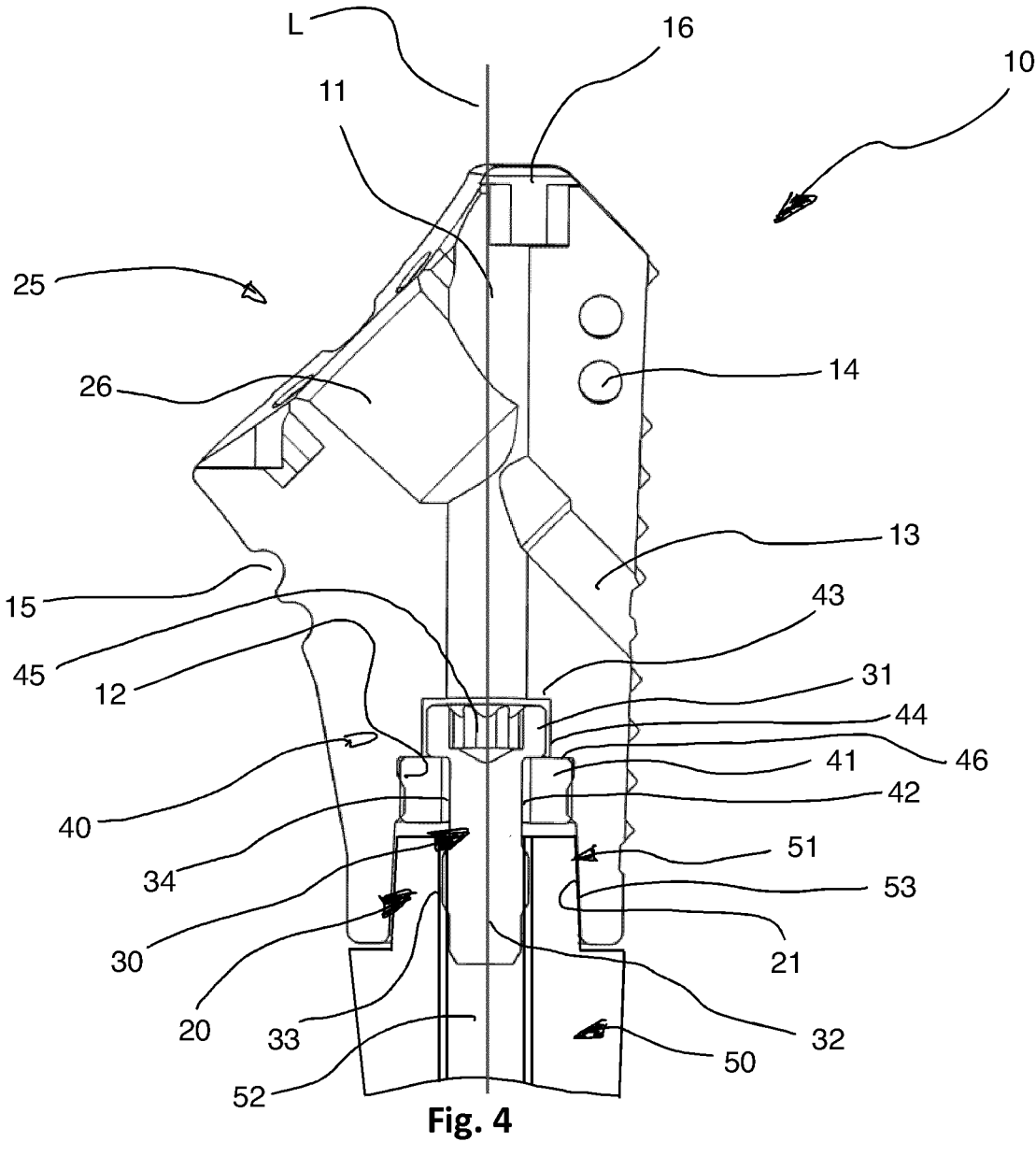
FIG. 4 is a cross-sectional view of the implant component shown in FIG. 3.

Further, the first implant component 10 comprises an assembly channel 11 that extends from the proximal end of the first implant component 10 (see FIG. 3) towards the distal end until the first interface part (see FIG. 4). As shown in FIG. 1, a fastening tool 70 may be inserted into the assembly channel 11 to fasten a second implant component 50 to the first implant component 10 using an assembly screw 30 (cf. FIG. 4) as will be described in more detail further below.

As shown in FIG. 3, the first implant component 10 may further comprise a handling tool engagement recess 16 that is provided at the proximal end of the first implant component 10 in order to handle this component prior or during surgery. In other word, the handling tool engagement recess 16 and/or the entrance to the assembly channel 11 is preferably located at the proximal side of the joint replacement component. This facilitates locating these structural features through the access wound of a surgical procedure.

The first implant component 10 of the exemplary embodiment shown in the figures also comprises one or more than one, and in particular two suture grooves 15. Further, the first implant component 10 may include suture holes 14. These suture holes 14 and suture grooves 15 are arranged at the circumference of the first implant component 10, preferably extending in a generally circumferential direction or direction parallel to a tangential of the circumference. The suture features is able to retain sutures for fixating soft tissue structures. Preferably, the suture holes 14 and/or suture grooves 15 are (generally uniformly) distributed around the circumference of the first implant component 10, i.e. about an axis in the direction of the longitudinal axis L (see FIG. 4).

The at least one suture groove 15 of the illustrated embodiment is further preferably formed as a longitudinal recess into the side of the first implant component 10 located radially opposite to an outer surface of this component that comprises an anchoring structure 17. The anchoring structure 17 at least hinders a relative movement between tissue in contact with this structure and the first implant component 10. It may be an integrated structure of the first implant component's body, a coating or a structure preferably added by means of additive manufacturing.

The first implant component 10 comprises a first interface part 20 located, for example, at the distal end of this component (see figures). It should be noted that the second interface part 25, i.e. in the illustrated embodiment the connection to the joint member 60 via the interface surface 26, may be based on the same principles that will be described in relation to the first interface part 20 in the following. Nonetheless, in the illustrated example, the connection between the first implant component and the joint member is established using a tapered connection that is tightened and locked via a fastening screw (not shown) inserted into a joint assembly channel 13. The joint assembly channel 13 extends from the tapered recess defined by the interface surface 26 along the longitudinal axis of this recess to the side opposite to the side, where the tapered recess is located. Preferably, the joint assembly channel 13 comprises a thread for an engagement with aforenoted fastening screw.

As described above, the first implant component 10 may have numerous structural features that are formed as recesses or cavities. In order to provide these structural features in one implant component, in particular the interface parts 20, 25 to other implant components (generally requiring the most space), these structural features are preferably designed to require less space.

This will be described in the following particularly in relation to the assembly channel 11 and the first interface part 20 that provide both a tight and secure connection as well as a compact build. This is best seen in the cross-section of the partly assembled joint replacement component 1 shown in FIG. 4, i. e. an implant component assembly. In this figure, the first interface part 20 employs an assembly screw 34 securing the attachment of a second implant component 50 to the first implant component 10. The second implant component 50 of this exemplary embodiment is an implant stem to be anchored within a prepared cavity of a patient's long bone (in the present embodiment a humerus).

As shown in FIG. 4, the interface surface 21 of the first interface part 20 is preferably defining a tapered interface surface for a tapered connection to the second implant component 50. Such a tapered connection has been proven to form a reliable connection to another implant component. However, in order to prevent any problems of an implant component connection, such as loosening or fretting, the present embodiment comprises the assembly screw 30. This assembly screw 30 allows to tighten the connection provided by the first interface part 20 to another implant component, such as the second implant component 50. In particular in case of a tapered connection, the assembly screw 30 provides a compressive connection force that ensures a permanent self-locking of the tapered connection. This is achieved by tightening the assembly screw 30 against a screw seat 41 forming part of a screw retention unit 40 with a predetermined torque. Such a predetermined tightening is generally not achieved by the usual technique of assembling a tapered connection using hammer blows.

For tightening, the second implant component 50 comprises an interface part 51 with an interface surface 53. The interface surface preferably forms a taper, in particular a conical taper, that corresponds to the first interface part 20. The interface part 51 further comprises a threaded hole 52, preferably a blind hole (not shown), extending in a proximal-distal direction and being aligned with the longitudinal axis L of the through hole 42 extending through the screw seat 41. The threaded hole 52 is formed for engaging a threaded portion 33 of the assembly screw 30. During tightening and locking the connection between the first implant component 10 and the second implant component 50, the second interface part 51 of the second implant component 50 is pulled into the first interface part 20 of the first implant component 10. Pulling the first interface part 20 and the second interface part towards each other allows a more guided and more stable assembly of the interface than hammer blows. It should be noted that the male and female interface parts 51 and 20 may be configured vice versa.

The screw seat 41 is preferably formed as a separate part for being mounted to the first implant component 10. In the embodiment shown in FIG. 4, the screw seat 41 is accommodated in an accommodation portion 12 formed adjacent and preferably directly adjacent to the interface surface 21 of the first interface part 20. In other words, the accommodation portion 12 is located further inside the first implant component 10 than the interface surface 21 as viewed from the first interface part 20. The accommodation portion is formed as part of the assembly channel 11 extending from the recess formed by the tapered interface surface 21 to the proximal and of the first implant component 10. Although preferably the interface part 20 and the assembly channel are aligned, they may also have a parallel offset. Nonetheless, in both cases they should be aligned so as to allow for pulling the interface parts and, thus, the implant components, towards each other.

As previously described, the screw seat 41 may be mounted to the first implant component 10 by a form fit and/or a friction fit. In the exemplary embodiment of FIG. 4, the screw seat 41 is inserted into the accommodation portion 12 and is tightened against a seat abutment step 46 or shoulder in the assembly channel 11 by a threaded engagement between the inner circumferential surface of the accommodation portion 12 and the outer circumferential surface of the screw seat 41. For tightening the screw seat 41, the screw seat 41 comprises preferably on the side facing the interface part 20 or second implant component 50 a tool engagement interface (not shown).

The side of the screw seat 41 facing away from the interface part 20 forms a support surface for the screw head 31 of the assembly screw 30. This side of the screw seat 41 is also the side abutting against aforenoted seat abutment step 46 of the assembly channel 11. At this location of the assembly channel 11, the diameter of the assembly channel 11 decreases from the diameter of the accommodation portion 12 to a diameter for accommodating the screw head 31. This diameter allows the screw head 31 to rotate about aforementioned longitudinal axis L for tightening and loosening the threaded engagement with the threaded hole 52 of the second implant component 50.

As previously noted, the screw seat 41 of the screw retention unit 40 may alternatively be integrally formed with the first implant component 10. In this case, the through hole 41 may have a thread (not shown) acting in the opposite direction in relation to the thread of the assembly screw's threaded portion 33. As noted above, the threaded portion 33 is for engagement with the threaded hole 51 of the second implant component 50. For example, the threaded portion 33 may have a right-hand thread whereas the thread of the screw seat's through hole 42 has a left-hand thread. For engaging the latter, the screw head 31 of the assembly screw 30 is also provided with a left-hand thread.

During assembly, the assembly screw 30 is inserted from the side of the first interface part 20 by screwing the left-hand thread of the screw head 31 into the left-hand threaded through hole of the screw seat 41. The screwing in of the screw head 31 is continued until the left-hand thread of the crew head 31 has completely passed and disengaged the left-hand threaded through hole. In this state, an unthreaded portion 34 of the assembly screw's screw shank 33 faces the left-hand thread without any engagement. This results in the assembly screw 31 being captured in the through hole 42 of the screw seat 41 between the left-hand thread of the screw head 31 and the right-hand thread of the screw shank's threaded portion 33. Further, the left-hand threads will not engage when the implant components 40 and 50 are fastened to each other. Instead, the left-hand thread of the screw head 31 will be supported by the left-hand thread of the screw seat 41. As the skilled person will appreciate, the left-hand threads from above may alternatively be provided as right-hand threads and vice versa.

As shown in FIG. 4, the assembly channel 11 further comprises a screw stop 43 that is formed as a step within the assembly channel 11. The screw stop 43 causes a decrease of the assembly channel's diameter that prevents the screw head 31 of the assembly screw 30 to pass through the adjacent part of the channel, i.e. in the embodiment of FIG. 4 the proximal part of the channel. The screw stop 43 and the screw seat 41 form a capture portion 44 within the assembly channel 11 for capturing the screw head 31. As a result, the screw retention unit 40 prevents the assembly screw 30 from passing through the assembly channel 11 in either direction.

More specifically, at the screw stop 43, the assembly screw 30 abuts with its end facing away from the interface part 20. At this end, the assembly screw 30 comprises a tool engagement interface 45 that is accessible for a fastening tool 70 from the side of assembly channel 11 opposite to the side of the assembly channel 11 opening towards the interface part 20. As described above, at the other end of the capture portion 44, the screw head 31 is supported by the surface of the screw seat 41 facing away from the interface part 20.

The extension of the capture portion 44 along the longitudinal axis L has a length that allows the assembly screw 30 to rotate about the longitudinal axis L and ensures that, in an assembled state, the screw shank 32 is passing through the through hole 42 of the screw seat 41. In particular, the length of the capture portion 44 of the assembly channel 11 is configured so that a threaded portion 33 of the screw shank 32 at least partly extends from the screw seat 41 on the side facing the second implant component 50 when the screw had 31 abuts against the screw stop 31.

As described above, the first implant component 10 preferably comprises in a direction along the longitudinal axis L from the interface surface 21 to an entrance of the assembly channel 11 for a fastening tool 70 the aforementioned features in the following sequence: a tapered recess defined by the interface surface 21 of the first interface part 20, an accommodation portion 12 for the screw seat 41, a capture portion 44 for the screw head 31 of the assembly screw 30, and the remainder of the assembly channel 11 until aforementioned entrance to the assembly channel 11 (situated in the present embodiment at the proximal end of the first implant component 10). It should be noted that in case of the interface part 20 formed as a male interface part, the screw seat 41 may be integrally formed with this interface part.

In the same direction, the interface part 20 and the assembly channel 11 have the following inner diameters relative to each other. In case of the interface surface 21 defining a recess, the inner diameter of this recess is larger than or basically equal to the inner diameter of the accommodation portion 12. In case of the interface surface 21 forming a protrusion, the screw seat 41 may be integrally formed with this protrusion. Further, the diameter of the accommodation portion 12 is larger than the diameter of the capture portion 44. The diameter of the capture portion 44 is in turn at least partly larger than the diameter of the remainder of assembly channel 11 up to the fastening tool entrance to this channel.

Such an arrangement of the interface part 20, the screw seat 41, the assembly screw 30, and the assembly channel 11 enhances the assembly and disassembly of a second implant component 50. More specifically, the assembly screw 30 ensures a tight connection between the first implant component 10 and the second implant component 50 as described above. By providing a secure and reliable connection, this connection is rather tight, which makes it hard to disassemble the implant components 10 and 50, in particular, if the interface surfaces 21, 53 or interface parts 20, 51 form a tapered connection. Here, capturing the assembly screw 30 and in particular the screw head 31 in the capture portion 44 results in pushing the second implant component 50 away from the first implant component 10 upon loosening the assembly screw 30. This is caused by the screw head 31 moving out of contact with the screw seat 41 and abutting against the screw stop 43. Once abutting the screw stop 43, further loosening the assembly screw 30 pushes the second implant component 50 further away via the engagement with the threaded hole 52. Consequently, the captured configuration of the assembly screw 30 advantageously assists in assembly and disassembly of the first and second implant components 10 and 50.

Further, this arrangement has the advantage that the assembly channel 11 can be configured with a smaller diameter while extending through the first implant component 10 since only the fastening tool has to pass this channel for engaging the tool interface recess instead of the screw head 31. This result in more freedom for the design of this component. In case of the present embodiment, numerous recesses and holes may be formed in the body of the first implant component 10 to provide this component with the desired functionality for the joint replacement.

For example, the embodiment of a first implant component 10 illustrated in the appended figures is configured to at least partly protrude from bone tissue and to serve as attachment structure for soft tissue structures surrounding our passing by the first implant component 10. Alternatively, the first implant component 10 may also be configured to be implanted into bone tissue without any attachment structure for soft tissue. As the skilled person will appreciate, for such an embodiment of the first implant component 10, the outer surface of this component may then be adapted for bone ingrowth or anchoring of the implant component via bone cement.

Further, the joint replacement component 1 of the exemplary embodiment is a shoulder joint replacement component for being attached to the humerus of a patient. However, the skilled person will appreciate that the above as well as the description following below may also be applied to joint replacements for other synovial joints of a patient, such as the synovial joints listed above.

At least the captured assembly screw 30 is preferably preassembled prior implantation of the first implant component 10. For this preassembly, the screw shank 32 of the assembly screw 30 is inserted into the through hole 42 of the screw seat 41. Then the assembly screw 30 and the screws seat are inserted into the recess defined by the interface surface 21 (or preferably together with the interface surface if this surface defines a protrusion) for engaging the accommodation portion 12. As described above, the engagement between the screw seat 41 and the engagement portion 12 is a threaded engagement in the illustrated exemplary embodiment. However, any other form of engagement such as a press fit or a snap fit is also possible. Preferably, the screw seat 41 abuts a seat abutment step within the assembly channel 11 to limit the extent of insertion of the screw seat 41. However, any other means for limiting insertion into the assembly channel 11 may be used to achieve this objective (e. g. limited thread, adhesive, pins, retaining ring, etc.). Once the screw seat 41 is fixed to the first implant component 10, the assembly screw 30 is captured within the capture portion 44 formed by the assembly channel 11 and the screw seat 41.

Preassembly may also include the assembly to a second implant component 50. For assembly to the second implant component 50, the interface part 51 of the second implant component 50 is brought into engagement with the first engagement part 20 of the first implant component 10. During this engagement, the assembly screw 30 is brought into engagement with the threaded through hole 52 of the second implant component 50 and is preferably tightened with a predetermined torque using a fastening tool 70 in order to provide a secure connection between the first implant component 10 and the second implant component 50. As previously described, the interface parts 20, 51 are preferably formed with tapered interface surfaces 21, 53, wherein one of these tapered interface surfaces faces radially outwards, whereas the other one of these tapered interface surfaces faces radially inwards.

Further, it may be necessary or at least advantageous to disassemble the first implant component 10 from the second implant component 50. Such a disassembly may become necessary if there is a change in an anatomic configuration such as a shortening or lengthening of soft tissue structures or due to overstuffing or impinging of soft tissue. The advantage of the implant component assembly in relation to the first implant component 10 and the connection enabled by this assembly to another implant component 50 is that a part of the joint replacement component 1 such as an implant stem, does not have to be removed but may be left anchored within the tissue of the patient. This has the advantage of preserving tissue and, thus, is gentler to the patient.

For a disassembly of the first implant component 10 and the second implant component 50, a fastening tool 70 is entered through aforementioned entrance into the assembly channel 11 like during fastening of the assembly screw 30 but is this time used for loosening and unscrewing the assembly screw 30 from the second implant component 50. As described above, this results in the assembly screw 30 pushing the first implant component 10 away from the second implant component 50. This pushing away action only takes place between the two implant components without using any surrounding tissue structures of the patient as support. This results in reduced stress and tissue damage for the patient in case of a revision of an implant component (such as the joint member 60 and/or the first implant component 10).

FIGS. 5 and 6 illustrate another embodiment of a joint replacement component 101 that makes use of a first implant component 10. This first implant component 10 is preferably configured as in any one of the embodiments described above. In difference to the embodiment shown in the previous figures and in particular in FIGS. 1 and 2, the joint member 160 has a different configuration than the joint member 60 shown in FIGS. 1 and 2. More specifically, the joint member 160 comprises an intermediate part 162 formed as an inclined inlay for receiving a joint part 161 including a concave joint surface 164. This configuration of a joint replacement component represents the humeral component of a reverse shoulder joints and preferably uses the same interface configuration as for an anatomic should joint replacement.

REFERENCE SIGNS

The following is a list of the last two digits of the reference signs used in the description and the drawings. As noted above and throughout the drawings, these reference signs refer to features that have the same or an equivalent function and/or structure.

1 joint replacement component
10 first implant component
11 assembly channel
12 accommodation portion
13 joint assembly channel
14 suture hole
15 suture groove
16 tool engagement recess
17 anchoring structure
20 first interface part 21 tapered interface surface
25 second interface part
26 interface surface
27 concave interface surface
28 indexing hole
30 assembly screw
31 screw head
32 screw shank
33 threaded portion
34 unthreaded portion
35 tool interface recess
40 screw retention unit
41 screw seat
42 through hole
43 screw stop
44 capture portion
45 tool engagement interface
46 seat abutment step
50 second implant component
51 interface part
52 threaded hole
53 interface surface
60 joint member
61 joint part
62 intermediate part
63 convex interface surface
65 joint fixation screw
70 fastening tool
L longitudinal axis
d1 diameter of the assembly channel
d2 diameter of the screw head

The invention claimed is:

1. An implant component assembly for a joint replacement, the assembly comprising:

an implant component, the implant component including an interface part configured for attaching to another implant component and an assembly channel, an assembly screw for securing the other implant component to the implant component, the assembly screw having a longitudinal axis, a screw head, and a screw shank and being insertable into the assembly channel, a screw retention unit configured for keeping the assembly screw within the assembly channel and allowing rotation of the assembly screw about the longitudinal axis, another interface part for attaching a joint member, wherein the another interface part comprises a tapered recess and a concave interface surface, wherein the concave interface surface comprises an array of indexing holes, a joint assembly channel that extends from the tapered recess along a longitudinal axis of the tapered recess to a side of the implant component opposite to the side of the implant component where the tapered recess is located, wherein the screw head is between the another interface part and the another implant component, wherein the screw retention unit includes a screw seat for supporting the screw head, the screw seat comprising a through hole for accommodating the screw shank, wherein the screw shank of the assembly screw comprises a threaded portion and an unthreaded portion, the unthreaded portion being located between the threaded portion and the screw head, and wherein the screw seat engages a portion of the screw shank having a reduced diameter in comparison to the threaded portion of the screw shank.

2. The implant component assembly of claim 1, wherein the assembly channel comprises an accommodation portion and the screw seat is insertable into the accommodation portion.

3. The implant component assembly of claim 2, wherein the screw seat is fixed within the accommodation portion by a form fit, friction fit, or welding.

4. The implant component assembly of claim 1, wherein the screw retention unit comprises a screw stop, the screw stop being formed as a step of the assembly channel.

5. The implant component assembly of claim 1, wherein a diameter of the assembly channel is smaller than a diameter of the screw head.

6. The implant component assembly of claim 1, wherein the screw retention unit comprises a screw stop, wherein a distance in the longitudinal direction between the screw seat and the screw stop is larger than the screw head in the longitudinal direction.

7. The implant component assembly of claim 1, wherein the interface part of the implant component comprises a tapered interface surface for mounting the other implant component, the tapered interface surface defining a recess.

8. The implant component assembly of claim 1, wherein the implant component further comprises at least one suture hole and/or at least one suture groove for securing soft tissue to the implant component.

9. The implant component assembly of claim 1, wherein the implant component further comprises a handling tool engagement recess for engaging a handling tool for handling the implant component during a surgical procedure.

10. The implant component assembly of claim 1, wherein the assembly screw comprises a tool interface recess formed for an engagement of a fastening tool in a rotational direction about the longitudinal axis of the assembly screw.

11. The implant component assembly of claim 1, wherein the array of indexing holes are arranged in a circle, wherein a center of the circle is located along the longitudinal axis of the tapered recess.

12. A method for pre-assembling an implant component assembly of a joint replacement, the method comprising the steps:

providing an implant component assembly for a joint replacement according to claim 1, wherein the assembly channel is formed as a through hole and extends from a proximal side of the implant component to the interface part;

providing the screw seat;

providing the assembly screw having the longitudinal axis, the screw head, and the screw shank;

inserting the screw shank of the assembly screw into the through hole of the screw seat to form an assembled screw seat;

inserting the assembled screw seat with the screw head first into an accommodation portion of the assembly channel from the side of the interface part; and fixing the screw seat within the accommodation portion of the assembly channel.

13. The method for pre-assembling of claim 12, further comprising the steps:

providing another implant component, the other implant component comprising an interface part corresponding to the interface part of the implant component and a threaded hole for engagement with the assembly screw;

connecting the implant components via their interface parts; and securing the implant components to each other via tightening the assembly screw.

* * * * *